United States Patent [19]

Takatsu et al.

[11] Patent Number: 5,178,794
[45] Date of Patent: Jan. 12, 1993

[54] ALKYLENE GLYCOL DERIVATIVE AND LIQUID CRYSTAL MIXTURE CONTAINING THE SAME

[75] Inventors: Haruyoshi Takatsu, Tokyo; Makoto Sasaki, Saitama; Kiyofumi Takeuchi, Tokyo, all of Japan

[73] Assignee: Dainippon Ink and Chemicals, Inc., Tokyo, Japan

[21] Appl. No.: 484,328

[22] Filed: Feb. 26, 1990

[30] Foreign Application Priority Data

| Mar. 1, 1989 | [JP] | Japan | 1-46656 |
| Mar. 1, 1989 | [JP] | Japan | 1-46657 |
| Mar. 7, 1989 | [JP] | Japan | 1-52790 |
| Mar. 27, 1989 | [JP] | Japan | 1-74737 |
| Apr. 14, 1989 | [JP] | Japan | 1-93015 |
| May 29, 1989 | [JP] | Japan | 1-132714 |
| Jun. 14, 1989 | [JP] | Japan | 1-149550 |

[51] Int. Cl.⁵ .................. C09K 19/30; C09K 19/12; C07C 41/00
[52] U.S. Cl. .................... 252/299.63; 252/299.66; 252/299.6; 568/631; 568/660; 568/664
[58] Field of Search ............... 568/631, 664, 660, 606, 568/607, 608, 609; 252/299.66, 299.63

[56] References Cited

U.S. PATENT DOCUMENTS

| 4,374,748 | 2/1983 | Inukai | 252/299.66 |
| 4,422,951 | 12/1983 | Sugimori et al. | 252/299.63 |
| 4,622,164 | 11/1986 | Eidenschink et al. | 252/299.63 |
| 4,724,097 | 2/1988 | Romer et al. | 252/299.63 |
| 4,808,333 | 2/1989 | Huynh-ba et al. | 252/299.66 |
| 4,857,227 | 8/1989 | Adams et al. | 252/299.65 |
| 4,868,341 | 9/1989 | Eidenschink et al. | 568/664 |
| 4,895,671 | 1/1990 | Ushioda et al. | 252/299.61 |
| 4,911,863 | 3/1990 | Sage et al. | 252/299.65 |
| 4,917,818 | 4/1990 | Sawada et al. | 252/299.61 |
| 4,923,632 | 5/1990 | Sawada et al. | 252/299.61 |

FOREIGN PATENT DOCUMENTS

| 0062470 | 10/1982 | European Pat. Off. . |
| 0249933 | 12/1987 | European Pat. Off. . |
| 0255700 | 2/1988 | European Pat. Off. . |
| 0278665 | 8/1988 | European Pat. Off. . |
| 1-022835 | 1/1989 | Japan | 568/664 |
| 8604081 | 7/1986 | PCT Int'l Appl. | 252/299.01 |
| 8705317 | 9/1987 | PCT Int'l Appl. | 252/299.01 |
| 2092146 | 8/1982 | United Kingdom . |
| 2108963 | 5/1983 | United Kingdom . |
| 8808870 | 11/1988 | World Int. Prop. O. . |

*Primary Examiner*—Robert L. Stoll
*Assistant Examiner*—C. Harris
*Attorney, Agent, or Firm*—Armstrong, Westerman, Hattori, McLeland and Naughton

[57] ABSTRACT

A compound represented by the following general formula (I).

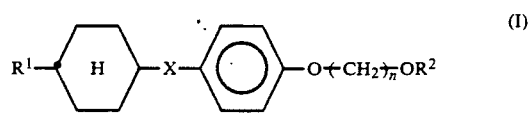

(I)

wherein $R^1$ and $R^2$ represent independently a straight-chain alkyl group having from 1 to 10 carbon atoms; X represents a direct bond, —CH₂CH₂—,

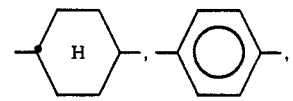

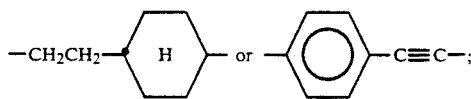

n represents an integer of from 1 to 5; and

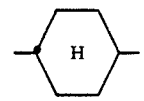

represents a cyclohexane ring in trans configuration. A nematic liquid crystal mixture containing a compound of formula (I) is also disclosed.

9 Claims, No Drawings

ALKYLENE GLYCOL DERIVATIVE AND LIQUID CRYSTAL MIXTURE CONTAINING THE SAME

FIELD OF THE INVENTION

This invention relates to alkylene glycol derivatives useful as electro-optical display materials and liquid crystal mixtures containing the same.

BACKGROUND OF THE INVENTION

Typical liquid crystal display cells include TN-LCD (twisted nematic liquid crystal display devices) which are utilized in the fields of clocks, watches, electronic calculators, pocket computers, word processors and personal computers. The information density on one display has been increased with an increase in information to be processed by OA apparatuses in recent years. Conventional TN-LCD can no longer meet the requirements of high multiplex drive systems, particularly word processors and personal computers with respect to the quality level of visual field angle and contrast.

Under such circumstances, STN (super twisted nematic) -LCD have been developed by Sheffer et al (SID '85 Digest, p. 120 (1985)) and Kinukawa et al. (SID '86 Digest, p. 122 (1986)) and are becoming wide spread for use in the display of high information processing in word processors and personal computers.

In a STN-LCD, the control of the angle formed by an aligning surface and a liquid crystal molecule, that is, a pertilt angle, is an important factor which has a significant effect on yields, etc. in the preparation of liquid crystal display cells.

Known orientation treatments include a method wherein the pretilt angle is controlled to a high pretilt angle of about 20° by oblique evaporation of SiOx. In practical application, there is known a method wherein the pretilt angle is controlled to about 5°, for example, by rubbing an organic film such as Sunever 150 (a product of Nissan Chemical Industries, Ltd.). Further, various aligning layers have been developed and are used to control the pretilt angle to 5° to 10° by rubbing method. It is known that the formation of a stripe domain becomes more difficult with an increase in pretilt angles, and yields in the preparation of liquid crystal cells are increased. However, there is much difficulty in preparing constantly stable aligning layers at a pretilt angle of 5° to 10° by rubbing method under the existing circumstances.

SUMMARY OF THE INVENTION

An object of the present invention is to provide novel liquid crystal compounds which can be perpendicularly aligned.

Another object of the present invention is to provide liquid crystal mixtures which can form a pretilt angle of greater than 5° when enclosed in liquid crystal cells having practically stable aligning layers capable of forming a pretilt angle of about 5° by rubbing.

The present invention provides, in one aspect, a compound represented by the following general formula (I).

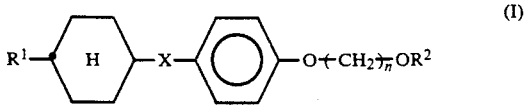

wherein $R^1$ and $R^2$ represent independently a straight-chain alkyl group having from 1 to 10 carbon atoms; X represents a direct bond, —CH$_2$CH$_2$—,

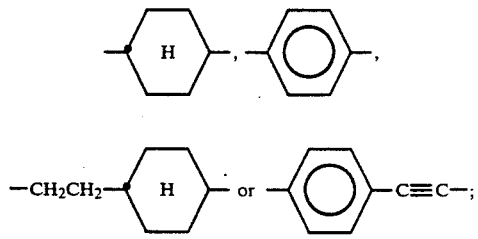

n represents an integer of from 1 to 5; and

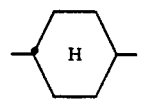

represents a cyclohexane ring in trans configuration.

The present invention provides in another aspect, a nematic liquid crystal mixture containing a compound represented by the formula (I).

DETAILED DESCRIPTION OF THE INVENTION

The compounds of formula (I) according to the present invention can be prepared by the following manufacturing procedure.

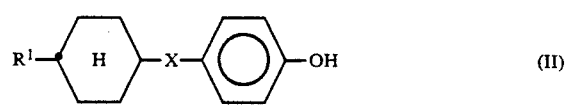

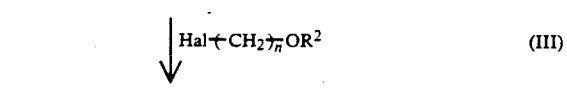

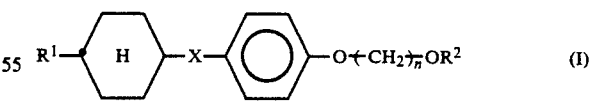

wherein Hal represents Cl or Br.

A compound of formula (II) is reacted with a compound of formula (III) in the presence of a strong base, such as potassium t-butoxide, in a polar solvent, such as dimethyl sulfoxide to prepare a compound of formula (I).

The transition temperatures of typical compounds of formula (I) prepared in the manner described above are given in Table 1.

TABLE 1

$$R^1-\underset{H}{\bigcirc}-X-\bigcirc-O(CH_2)_n OR^2$$

| No. | $R^1$ | X | n | $R^2$ | Phase transition temperature |
|---|---|---|---|---|---|
| 1 | n-$C_3H_7$— | direct bond | 2 | —$CH_3$ | 45(C→I) 19(I⇌N) |
| 2 | n-$C_3H_7$— | —$CH_2CH_2$— | 2 | —$CH_3$ | 28(C→I) 25(I⇌N) |
| 3 | n-$C_3H_7$— | —⟨H⟩— | 1 | —$CH_3$ | 33(C→S) 156(S⇌I) |
| 4 | n-$C_4H_9$— | —⟨H⟩— | 1 | —$CH_3$ | 45(C→S) 171(S⇌I) |
| 5 | n-$C_5H_{11}$— | —⟨H⟩— | 1 | —$CH_3$ | 38(C→S) 173(S⇌I) |
| 6 | n-$C_3H_7$— | —⟨H⟩— | 1 | —$C_2H_5$ | S at room temp. 144(S⇌I) |
| 7 | n-$C_3H_7$— | —⟨H⟩— | 2 | —$CH_3$ | 65(C→S) 169(S⇌N) 196(N⇌I) |
| 8 | n-$C_5H_{11}$— | —⟨H⟩— | 2 | —$CH_3$ | 95(C→S) 188(S⇌N) 197(N⇌I) |
| 9 | n-$C_3H_7$— | —⟨H⟩— | 2 | —$C_2H_5$ | 36(C→S) 166(S⇌N) 176(N⇌I) |
| 10 | n-$C_3H_7$— | —⟨H⟩— | 2 | -n-$C_3H_5$ | 85(C→S) 155(S⇌N) 163(N⇌I) |
| 11 | n-$C_3H_7$— | —⟨⌾⟩— | 2 | —$CH_3$ | 103(C→S) 158(S⇌N) 199(N⇌I) |
| 12 | n-$C_3H_7$— | —$CH_2CH_2$—⟨H⟩— | 1 | —$CH_3$ | 54(C→S) 147(S⇌N) 164(N⇌I) |
| 13 | n-$C_3H_7$— | —⟨⌾⟩—C≡C— | 2 | —$CH_3$ | 106(C→S) 227(N⇌I) |

In Table 1, C represents crystal phase, S represents smectic phase, N represents nematic phase and I represents isotropic phase.

Preferred examples of liquid crystal compounds which can be used in combination with the compounds of formula (I) include 4'-substituted phenyl esters of 4-substituted benzoic acids, 4'-substituted phenyl esters of 4-substituted cyclohexanecarboxylic acids, 4'-substituted biphenyl esters of 4-substituted cyclohexanecarboxylic acids, 4'-substituted phenyl esters of 4-(4-substituted cyclohexanecarbonyloxy)benzoic acids, 4'-substituted phenyl esters of 4-(4-substituted cyclohexyl)-benzoic acids, 4'-substituted cyclohexyl esters of 4-(4-substituted cylohexyl)benzoic acids, 4-substituted-4'-substituted biphenyls, 4-substituted phenyl-4'-substituted cyclohexanes, 4-substituted-4"-substituted terphenyls, 4-substituted biphenyl-4'-substituted cyclohexanes and 2-(4-substituted phenyl)-5-substituted pyrimidines.

A liquid crystal mixture consisting of 60 wt % of a liquid crystal mixture (A) (which is widely used as a nematic liquid crystal material), 20 wt % of the compound No. 1 or No. 2 given in Table 1 and 20 wt % of the compound No. 7 given into Table 1, was filled in a liquid crystal display cell wherein aligning layers on glass surface prepared by rubbing organic aligner Sunever 150 (a product of Nissan Chemical Industries, Ltd.) (which was considered to be an organic aligning layer giving a pretilt angle of about 5°) were oppositely arranged in parallel in an up and down relationship. Pretilt angle was measured by the magnetic potential method. For the purpose of comparison, each of the liquid crystal mixture (A) alone and a liquid crystal mixture consisting of 60 wt % of the liquid crystal liquid (A), 20 wt % of compound (a) or (b) having a similar chemical structure to that of the compound of formula (I) according to the present invention and 20 wt % of the compound No. 7, was enclosed in said cell. Pretilt angle was measured. The results are shown in Table 2.

The liquid crystal mixture (A) consisted of the following compounds.

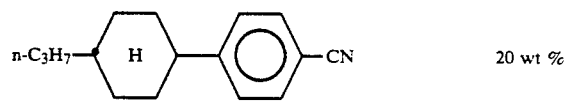

20 wt %

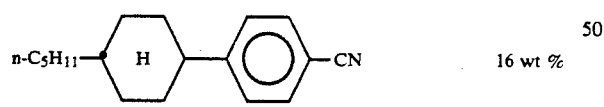

16 wt %

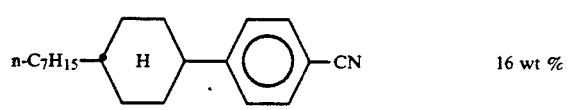

16 wt %

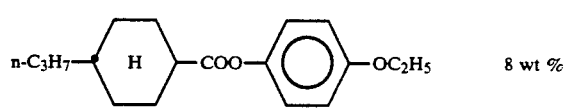

8 wt %

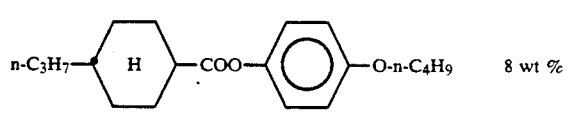

8 wt %

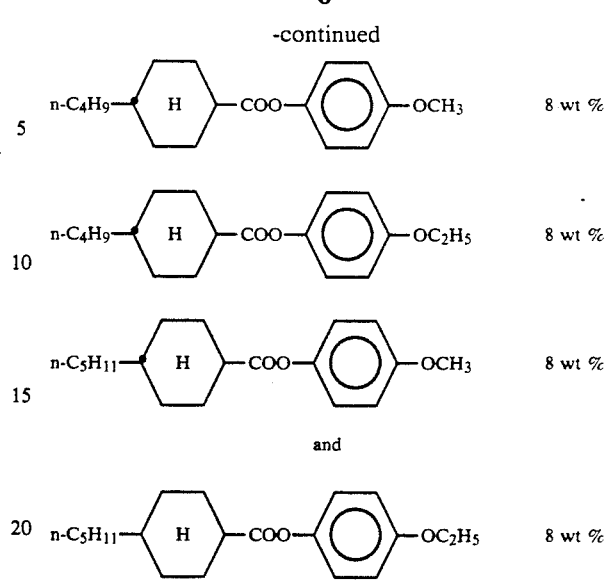

and 8 wt %

The liquid crystal mixture (A) had the following physical properties.

| N-I Transition temperature | 54.5° C. |
|---|---|
| Viscosity (20° C.) | 21.0 c.p. |
| Optical anisotropy (Δn) | 0.0917 |
| Dielectric anisotropy (Δε) | 6.5 |
| Threshold voltage | 1.60 V |

The compounds (a) and (b) are represented by the following formulas.

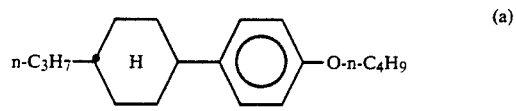

(a)

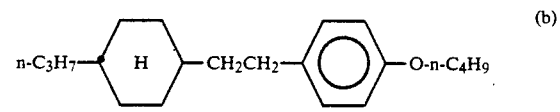

(b)

TABLE 2

| Liquid Crystal Mixture | Pretilt Angle |
|---|---|
| (A) | 4.8° |
| (A) + No. 1 + No. 7 | 6.7° |
| (A) + No. 2 + No. 7 | 6.7° |
| (A) + (a) + No. 7 | 6.0° |
| (A) + (b) + No. 7 | 6.2° |

It is apparent from the data of Table 2 that when the liquid crystal mixture contains the compound No. 1 or No. 2 of the present invention, the rate of increase in pretilt angle is high in comparison with the liquid crystal mixture containing the compound (a) or (b), though any of the liquid crystal mixtures containing the compound No. 7 shows an increase in pretilt angle by at least 1°.

A liquid crystal mixture consisting of 80 wt % of the liquid crystal mixture (A) and 20 wt % of the compound No. 3, NO. 4, No. 5, No. 6, No. 7, No. 8, No. 9, No. 10, No. 11, No. 12 or No. 13 given in Table 1 was filled into the same liquid crystal display cell used in liquid crystal mixtures in Table 2. Pretilt angle was measured. For the purpose of comparison, a liquid crystal mixture consisting of 80 wt % of the liquid crystal mixture (A) and 20 wt % of a compound (c), (d), (e) or (f) having a similar chemical structure to that of the compound of formula (I) according to the present invention was filled into the liquid crystal display cell. Pretilt angle was measured. The results are shown in Table 3.

The compounds (c) to (f) are represented by the following formulas.

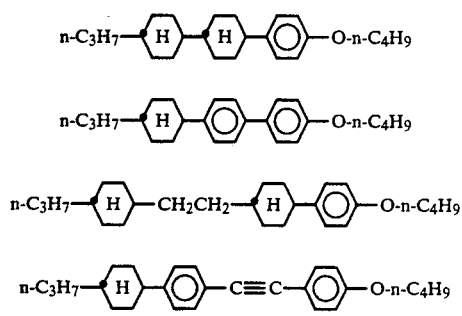

TABLE 3

| Liquid Crystal Mixture | Pretilt Angle |
| --- | --- |
| (A) | 4.8° |
| (A) + No. 3 | 6.1° |
| (A) + No. 4 | 6.1° |
| (A) + No. 5 | 6.0° |
| (A) + No. 6 | 6.0° |
| (A) + No. 7 | 6.2° |
| (A) + No. 8 | 6.3° |
| (A) + No. 9 | 6.1° |
| (A) + No. 10 | 6.0° |
| (A) + No. 11 | 6.0° |
| (A) + No. 12 | 6.2° |
| (A) + No. 13 | 5.8° |
| (A) + (c) | 5.0° |
| (A) + (d) | 5.0° |
| (A) + (e) | 4.9° |
| (A) + (f) | 4.7° |

It can be understood from the data of Table 3 that when the liquid crystal mixtures contain the compounds of formula (I), the pretilt angle can be increased by at least 1° and that the liquid crystal mixtures containing the compounds of formula (I) can form pretilt angles which are larger by at least 1° than those formed by the liquid crystal mixtures containing the compounds which are known to be useful for a STN-LCD and have a similar chemical structure to that of the compound of formula (I). The formation of a stripe domain is made very difficult by a difference in pretilt angle of 1°, and yields in the preparation of STN liquid crystal display cells are improved. Further, it has been confirmed that the compounds of formula (I) in the nematic state have uniform perpendicular alignment on glass surface.

Further, a liquid crystal mixture (B) consisting of 50 wt % of the compound No. 1 and 50 wt % of the compound No. 7 and a liquid crystal mixture (C) consisting of 50 wt % of the compound No. 2 and 50 wt % of the compound No. 7 were prepared. The compounds No. 1 and No. 2 are each a monotropic liquid crystal and the compound No. 7 shows a nematic phase at 169° to 196° C. as shown in Table 1. However, both the liquid crystal mixture (B) and the liquid crystal mixture (C) show a nematic phase at 49° to 101° C. and at 50° to 102° C. respectively. They show nematic phases in the supercooled state. Accordingly, it can be understood that the compounds No. 1 and No. 2 are well-soluble with the compound No. 7, because the lower temperature of nematic phase is greatly lowered and the temperature range is widened.

Further, a room temperature nematic liquid crystal consisting of 80 wt % of the liquid crystal mixture (B) or (C) and 20 wt % of the following liquid crystal mixture (D) was filled into a liquid crystal display cell which was not subjected to aligning layers. It could be confirmed that they had uniform perpendicular alignment.

The liquid crystal mixture (D) consisted of perpendicular alignment.

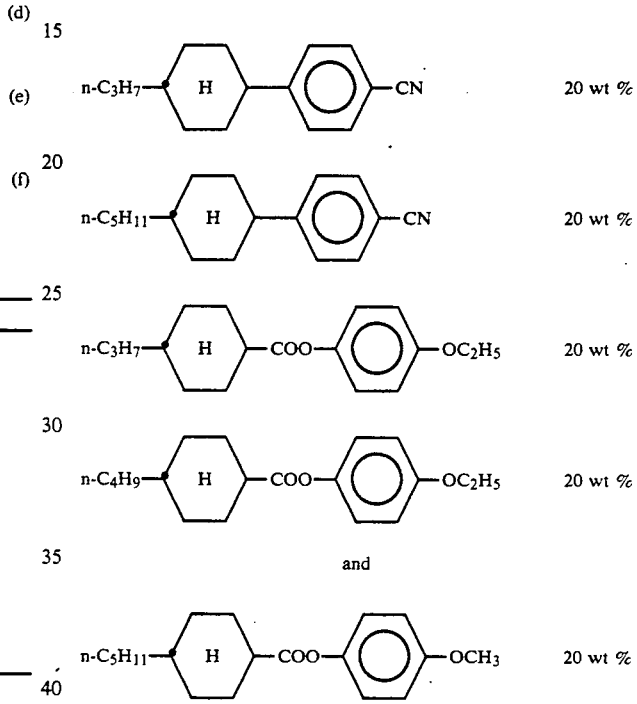

and

The liquid crystal mixture (D) had the following physical properties.

| N-I Transition temperature | 56.5° C. |
| --- | --- |
| Viscosity (20° C.) | 20.5 c.p. |
| Optical anisotropy (Δn) | 0.094 |
| Dielectric anisotropy (Δε) | 5.8 |
| Threshold voltage | 1.65 V |

The compounds of the present invention are characterized in that the pretilt angles can be increased when they are mixed in conventional liquid crystals. However, the use thereof is not limited to liquid crystal display cells having a pretilt angle of about 5°. Further, the perpendicularly alignable liquid crystal compounds of the present invention are very useful for ECB (birefringence control) system display devices which require perpendicular alignment.

The present invention is illustrated in greater detail by reference to the following examples which, however, are not to be construed as limiting the invention in any way.

EXAMPLE 1

10 9 g (0.050 mol) of the compound of formula

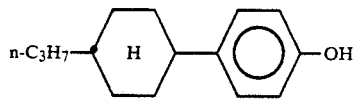

was dissolved in a mixed solution of 100 ml of dimethyl sulfoxide and 25 ml of tetrahydrofuran. While stirring the solution at room temperature, 7.5 g (0.066 mol) of potassium t-butoxide was added thereto. The mixture was continuously stirred for 30 minutes. 7.2 g (0.075 mol) of the compound of formula ClCH$_2$CH$_2$OCH$_3$ was added thereto. The mixture was reacted at 50° C. for 3 hours.

After the completion of the reaction, 150 ml of 9% hydrochloric acid was added thereto. Extraction was carried out with 100 ml of ethyl acetate three times. The organic layer was washed with water and dried over anhydrous sodium sulfate. The solvent was distilled off under reduced pressure. The residue was recrystallized from 200 ml of methanol to obtain 10.5 g (0.038 mol) of the following compound.

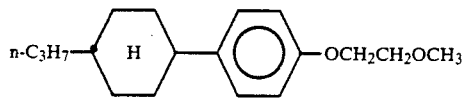

Phase transition temperature 45° C. (C→I)
19° C. (I⇌N)

EXAMPLE 2

The procedure of Example 1 was repeated except that 12.3 g (0.050 mol) of the compound of formula

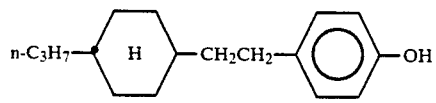

was used in place of the compound of formula

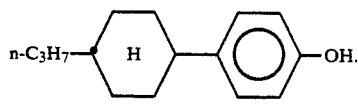

There was obtained 12.5 g (0.041 mol) of the following compound.

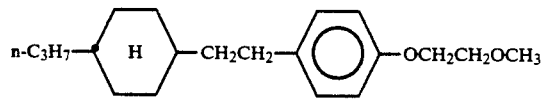

Phase transition temperature 28° C. (C→I)
25° C. (I⇌N)

EXAMPLE 3

6 g (0.020 mol) of the compound of formula

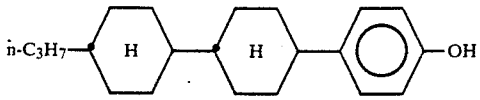

was dissolved in a mixed solution of 50 ml of dimethyl sulfoxide and 15 ml of tetrahydrofuran. While stirring the solution at room temperature, 2.5 g (0.022 mol) of potassium t-butoxide was added thereto. The mixture was continuously stirred for 30 minutes. 2.0 g (0.025 mol) of the compound of formula ClCH$_2$OCH$_3$ was added thereto and the mixture was reacted at room temperature for 2 hours.

After the completion of the reaction, 50 ml of 9% hydrochloric acid was added thereto. Extraction was carried out with 80 ml of ethyl acetate three times. The organic layer was washed with water and dried over anhydrous sodium sulfate. The solvent was distilled off under reduced pressure. The residue was recrystallized from 120 ml of ethanol to obtain 5.7 g (0.017 mol) of the following compound.

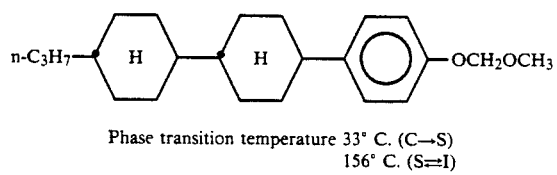

Phase transition temperature 33° C. (C→S)
156° C. (S⇌I)

EXAMPLE 4

In the same manner as in Example 3, the following compound was obtained.

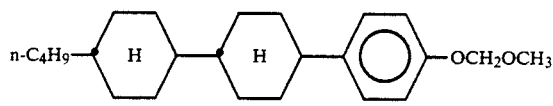

Phase transition temperature 45° C. (C→S)
171° C. (S⇌I)

EXAMPLE 5

In the same manner as in Example 3, the following compound was obtained.

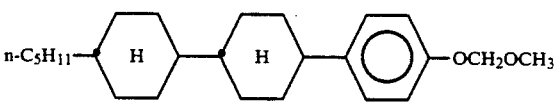

Phase transition temperature 38° C. (C→S)
173° C. (S⇌I)

EXAMPLE 6

In the same manner as in Example 3, the following compound was obtained.

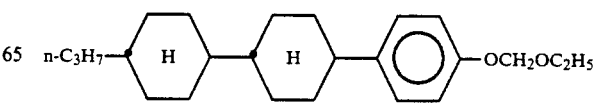

Phase transition temperature

-continued at room temperature    S
                       144° C. (S⇌I)

EXAMPLE 7

The procedure of Example 3 was repeated except that 2.4 g (0.025 mol) of the compound of formula ClCH₂CH₂OCH₃ was used in place of the compound of formula ClCH₂OCH₃. There was obtained 6.1 g (0.017 mol) of the following compound.

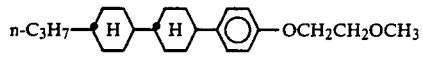

Phase transition temperature 65° C. (C→S)
                             169° C. (S⇌N)
                             196° C. (N⇌I)

EXAMPLE 8

In the same manner as in Example 7, the following compound was obtained.

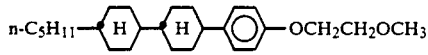

Phase transition temperature 95° C. (C→S)
                             188° C. (S⇌N)
                             197° C. (N⇌I)

EXAMPLE 9

In the same manner as in Example 7, the following compound was obtained.

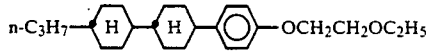

Phase transition temperature 36° C. (C→S)
                             166° C. (S⇌N)
                             176° C. (N⇌I)

EXAMPLE 10

In the same manner as in Example 7, the following compound was obtained.

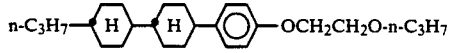

Phase transition temperature 85° C. (C→S)
                             155° C. (S⇌N)
                             163° C. (N⇌I)

EXAMPLE 11

The procedure of Example 1 was repeated except that 14.7 g (0.050 mol) of the compound of formula

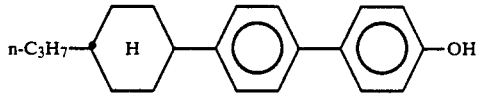

was used in place of the compound of formula

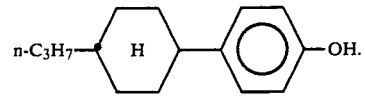

There was obtained 12.5 g (0.036 mol) of the following compound.

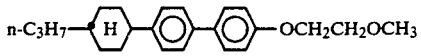

Phase transition temperature 103° C. (C→S)
                             158° C. (S⇌N)
                             199° C. (N⇌I)

EXAMPLE 12

The procedure of Example 3 was repeated except that 6.6 g (0.020 mol) of the compound of formula

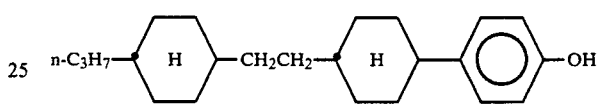

was used in place of the compound of formula

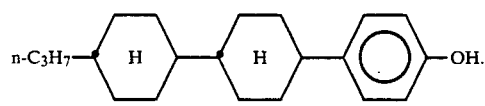

There was obtained 5.7 g (0.015 mol) of the following compound.

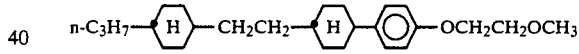

Phase transition temperature  54° C. (C→S)
                             147° C. (S⇌N)
                             164° C. (N⇌I)

EXAMPLE 13

The procedure of Example 1 was repeated except that 6.4 g (0.020 mol) of the compound of formula

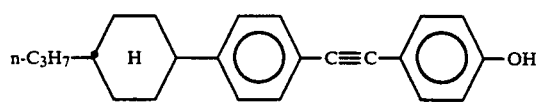

was used in place of formula

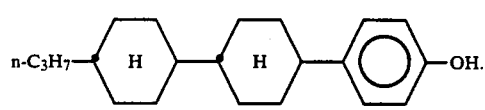

There was obtained 5.5 g (0.015 mol) of the following compound.

-continued

Phase transition temperature 106° C. (C→N)
227° C. (N⇌I)

EXAMPLE 14

A liquid crystal mixture (A) consisted of n-C$_3$H$_7$—⟨H⟩—⟨◯⟩—CN   20 wt % n-C$_5$H$_{11}$—⟨H⟩—⟨◯⟩—CN   16 wt % n-C$_7$H$_{15}$—⟨H⟩—⟨◯⟩—CN   16 wt % n-C$_3$H$_7$—⟨H⟩—COO—⟨◯⟩—OC$_2$H$_5$   8 wt % n-C$_3$H$_7$—⟨H⟩—COO—⟨◯⟩—O-n-C$_4$H$_9$   8 wt % n-C$_4$H$_9$—⟨H⟩—COO—⟨◯⟩—OCH$_3$   8 wt % n-C$_4$H$_9$—⟨H⟩—COO—⟨◯⟩—OC$_2$H$_5$   8 wt % n-C$_5$H$_{11}$—⟨H⟩—COO—⟨◯⟩—OCH$_3$   8 wt % and n-C$_5$H$_{11}$—⟨H⟩—COO—⟨◯⟩—OC$_2$H$_5$   8 wt %

The liquid crystal mixture 9A) had the following physical properties.

| N-I Transition temperature | 54.5° C. |
| Viscosity (20° C.) | 21.0 c.p. |
| Optical anisotropy ($\Delta n$) | 0.0917 |
| Threshold voltage | 1.60 V |

A liquid crystal mixture consisting of 20 wt % of the compound obtained in Example 1, 20 wt % of the compound obtained in Example 7 and 60 wt % of the liquid crystal mixture (A) was prepared. The physical properties thereof were measured. The following measured values were obtained.

| N-I Transition temperature | 70.1° C. |
| Viscosity (20° C.) | 22.4 c.p. |
| Optical anisotropy ($\Delta n$) | 0.0960 |
| Dielectric anisotropy ($\Delta \epsilon$) | 4.8 |
| Threshold voltage | 2.15 V |

The liquid crystal mixture was filled in a liquid crystal cell wherein aligning layers on glass surface prepared by rubbing Sunever 150 were oppositely arranged in parallel. Pretilt angle was measured. It was 6.7°.

EXAMPLE 15

A liquid crystal mixture was prepared in the same manner as in Example 14 except that 20 wt % of the compound obtained in Example 2 was used in place of the compound obtained in Example 1. The physical properties thereof were measured. The following measured values were obtained.

| N-I Transition temperature | 71.2° C. |
| Viscosity (20° C.) | 22.5 c.p. |
| Optical anisotropy ($\Delta n$) | 0.0970 |
| Dielectric anisotropy ($\Delta \epsilon$) | 4.8 |
| Threshold voltage | 2.17 V |

In the same manner as in Example 14, pretilt angle was measured. It was 6.7°

EXAMPLES 16 TO 24

A liquid crystal mixture consisting of 20 wt % of the compound obtained in Example 3, 4, 5, 6, 7, 8, 11, 12 or 13 and 80 wt % of the liquid crystal mixture (A) was prepared. The physical properties thereof were measured. Further, pretilt angle was measured in the same manner as in Example 14, The results are shown in Table 4.

TABLE 4

| Example | N-I Transition Temperature (°C.) | Viscosity (20° C.) (c.p.) | Optical Anisotropy ($\Delta n$) | Dielectric Anisotropy ($\Delta \epsilon$) | Threshold Voltage (V) | Pretilt Angle (°) |
|---|---|---|---|---|---|---|
| 14 | 70.1 | 22.4 | 0.0960 | 4.8 | 2.15 | 6.7 |
| 15 | 71.2 | 22.5 | 0.0970 | 4.8 | 2.17 | 6.7 |
| 16 | 67.7 | 24.9 | 0.0953 | 6.1 | 1.85 | 6.1 |
| 17 | 66.9 | 26.2 | 0.0938 | 5.8 | 1.76 | 6.1 |
| 18 | 69.0 | 26.3 | 0.0947 | 5.9 | 1.82 | 6.0 |
| 19 | 63.6 | 26.0 | 0.0930 | 5.7 | 1.78 | 6.0 |
| 20 | 79.5 | 25.1 | 0.1010 | 6.1 | 2.01 | 6.2 |
| 21 | 79.6 | 26.3 | 0.1010 | 5.9 | 2.02 | 6.2 |
| 22 | 79.0 | 25.2 | 0.1130 | 6.2 | 1.93 | 6.0 |
| 23 | 76.2 | 24.0 | 0.0995 | 6.22 | 1.84 | 6.2 |

TABLE 4-continued

| Example | N-I Transition Temperature (°C.) | Viscosity (20° C.) (c.p.) | Optical Anisotropy (Δn) | Dielectric Anisotropy (Δε) | Threshold Voltage (V) | Pretilt Angle (°) |
| --- | --- | --- | --- | --- | --- | --- |
| 24 | 82.3 | 26.1 | 0.1250 | 6.2 | 2.05 | 5.8 |

The compounds of formula (I) according to the present invention have themselves perpendicular alignment properties. When nematic liquid crystal mixtures containing the compounds of formula (I) together with conventional nematic liquid crystal mixtures are filled in the liquid crystal display cells having aligning layers capable of forming a pretilt angle of about 5°, the pretilt angle can be increased.

Accordingly, the compounds of formula (I) according to the present invention are very useful in the preparation of a STN-LCD.

While the invention has been described in detail and with reference to specific embodiments thereof, it will be apparent to one skilled in the art that various changes and modifications can be made therein without departing from the spirit and scope thereof.

What is claimed is:

1. A compound represented by the following general formula (I).

R¹—⟨H⟩—X—⟨○⟩—O(CH₂)ₙOR²    (I)

wherein R¹ and R² represent independently a straight-chain alkyl group having from 1 to 10 carbon atoms; X represents a direct bond, —CH₂CH₂—,

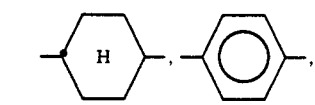,

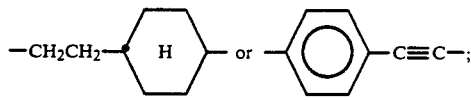;

n represents an integer of from 1 to 5; and

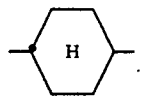

represents a cyclohexane ring in trans configuration.

2. A compound as claimed in claim 1, wherein X is a direct bond.

3. A compound as claimed in claim 1, wherein X is —CH₂CH₂—.

4. A compound as claimed in claim 1, wherein X is

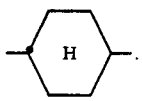

5. A compound as claimed in claim 1, wherein X is

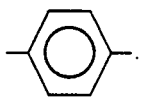

6. A compound as claimed in claim 1, wherein X is

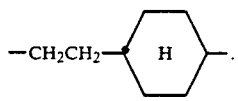

7. A compound as claimed in claim 1, wherein X is

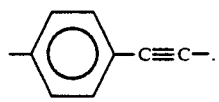

8. A nematic liquid crystal mixture containing a compound as claimed in claim 1.

9. A nematic liquid crystal composition having added thereto at least one compound as claimed in claim 1 having an increased pretilt angle as compared to the pretilt angle of the composition in the absence of said added compound.

* * * * *